US007867262B2

(12) United States Patent
Morales et al.

(10) Patent No.: US 7,867,262 B2
(45) Date of Patent: Jan. 11, 2011

(54) SURGICAL FIXING DEVICE FOR TWO BONE PARTS

(75) Inventors: Pedro Morales, Tuttlingen (DE); Dieter Weisshaupt, Immendingen (DE); Manfred Dworschak, Duerbheim (DE); Theodor Lutze, Balgheim (DE)

(73) Assignee: Aesculap AG, Tuttlingen (DE)

( * ) Notice: Subject to any disclaimer, the term of this patent is extended or adjusted under 35 U.S.C. 154(b) by 697 days.

(21) Appl. No.: 11/787,113

(22) Filed: Apr. 12, 2007

(65) Prior Publication Data

US 2007/0270856 A1   Nov. 22, 2007

(30) Foreign Application Priority Data

Apr. 28, 2006 (DE) .................. 10 2006 021 025

(51) Int. Cl.
*A61B 17/56* (2006.01)
*A61B 17/68* (2006.01)
*A61B 17/80* (2006.01)
*A61B 17/82* (2006.01)

(52) U.S. Cl. .................. 606/281; 606/70; 606/71; 606/75; 606/280; 606/286; 606/324; 606/331; 606/298; 606/99; 606/104

(58) Field of Classification Search .................. 606/70, 606/71, 99, 104, 79, 280, 281, 286, 75, 298, 606/324, 331, 907, 916, 908
See application file for complete search history.

(56) References Cited

U.S. PATENT DOCUMENTS 4,279,248 A   7/1981   Gabbay

| 4,670,938 A | 6/1987 | Fowlston |
| 4,802,477 A | 2/1989 | Gabbay |
| 5,549,620 A | 8/1996 | Bremer |

(Continued)

FOREIGN PATENT DOCUMENTS

DE   19634696   *   8/1996

(Continued)

OTHER PUBLICATIONS

Patent Abstracts of Japan, vol. 2003, No. 06, "Sacrum Fixing Device", Publication No. 2003038504, Publication Date Feb. 12, 2003.

*Primary Examiner*—Thomas C Barrett
*Assistant Examiner*—Sameh Boles
(74) *Attorney, Agent, or Firm*—Lipsitz & McAllister, LLC (57) ABSTRACT

A surgical fixing device for the fixing of adjacent bone parts is provided. A first engaging element is provided for engaging the underside of the two bone parts and a second engaging element is provided for engaging the upper side of the bone parts. A tensioning device connects the two engaging elements to each other through an interspace between the bone parts and permanently fixes the two engaging elements with respect to each other in a tensioned manner when they engage the underside and the upper side of the bone parts. To make it easier to apply the fixing device, at least one elastic tensioning element is provided which displaces a supporting surface applied to the upper side of the bone parts toward the first engaging element, so that the supporting surface and the first engaging element can be moved away from each other against the force of the elastic tensioning element.

20 Claims, 9 Drawing Sheets

U.S. PATENT DOCUMENTS

| | | |
|---|---|---|
| 5,620,452 A | 4/1997 | Yoon |
| 5,722,976 A | 3/1998 | Brown |
| 5,729,867 A | 3/1998 | Carmichael |
| 5,800,436 A | 9/1998 | Lerch |
| 6,022,351 A | 2/2000 | Bremer et al. |
| 6,045,552 A | 4/2000 | Zucherman et al. |
| 7,361,178 B2 * | 4/2008 | Hearn et al. ............... 606/281 |
| 2005/0065521 A1 | 3/2005 | Steger et al. |
| 2005/0278027 A1 | 12/2005 | Hyde, Jr. |
| 2006/0122611 A1 | 6/2006 | Morales et al. |
| 2007/0038218 A1 | 2/2007 | Grevious |
| 2007/0250059 A1 | 10/2007 | Weisshaupt et al. |

FOREIGN PATENT DOCUMENTS

| | | | |
|---|---|---|---|
| DE | 299 19 090 | | 1/2000 |
| DE | 203 15 612 | | 1/2004 |
| DE | 103 26 690 | | 1/2005 |
| DE | 10 2004 038 823 | | 3/2006 |
| EP | 0 014 823 | | 9/1980 |
| EP | 02/09602 | | 2/2002 |
| JP | 2003-220070 | | 8/2003 |
| WO | WO2004107998 | * | 6/2003 |
| WO | 2004/006783 | | 1/2004 |
| WO | 2004/016205 | | 2/2004 |
| WO | 2006/002744 | | 1/2006 |

* cited by examiner

SURGICAL FIXING DEVICE FOR TWO BONE PARTS

This application claims the benefit of German patent application no. 10 2006 021 025.5 filed on Apr. 28, 2006, which is incorporated herein and made a part hereof by reference.

BACKGROUND OF THE INVENTION

The invention relates to a surgical fixing device for the mutual fixing of two bone parts lying next to each other, having a first engaging element for engaging the underside of the two bone parts and having a second engaging element for engaging the upper side of the bone parts and having a tensioning device, which connects the two engaging elements to each other through an interspace between the bone parts and which permanently fixes the two engaging elements with respect to each other in a tensioned manner when they engage the underside and the upper side of the bone parts.

Such a fixing device is known for example from DE 103 26 690 B4. With fixing devices of this type, two bone parts lying next to each other, for example two bone parts of the cranial bone or the sternum, can be fixed while lying side by side, leaving between the two bone parts a very narrow interspace through which the two engaging elements are tensioned with respect to each other.

It is difficult for such a device to be applied, since on the one hand the two engaging elements must be positioned on the underside and on the upper side of the bone parts and since on the other hand the two bone parts also have to be appropriately brought together. This can lead to problems in particular when engaging elements that have to be implanted in a specific direction are used, for example in the case of elongate, rectangular engaging elements.

It is an object of the invention to form a surgical fixing device of the generic type in such a way as to make it easier for the fixing device to be applied.

SUMMARY OF THE INVENTION

This object is achieved according to the invention in the case of a surgical fixing device of the type described at the beginning by the fixing device comprising at least one elastic tensioning element, which displaces a supporting surface which can be applied to the upper side of the bone parts toward the first engaging element, so that the supporting surface and the first engaging element can be moved away from each other against the force of the elastic tensioning element.

Such a configuration makes it possible before the bone parts are brought together to fix the surgical fixing device on one of the two bone parts in such a way that the engaging element assumes the correct position, but does not yet tension the bone parts with respect to each other with the final force. With this first engagement of the fixing device on one of the two bone parts, the first engaging element is drawn toward the underside of the bone part by the elastic tensioning element, while the supporting surface elastically engages the upper side of this bone part. The supporting surface and the first engaging element consequently accommodate the first bone part elastically between them and keep the fixing device in this position on the first bone part. It is then possible to push the second bone part laterally between the first engaging element and the supporting surface, optionally with elastic widening of the interspace between the first engaging element and the supporting surface, and only then are the first engaging element and the second engaging element finally tensioned with respect to each other.

In the case of a first preferred embodiment of the invention, it is provided that the supporting surface is part of the elastic tensioning element. In this case, it may be provided in particular that the supporting surface is disposed between the two engaging elements before the fixing device is applied to the bone parts. It is advantageous if the elastic tensioning element is releasably connected to the fixing device. After the fixing device is applied for the first time and after the second bone part is pushed in between the first engaging element and the supporting surface, it is therefore possible to remove the elastic tensioning element and then tension the two engaging elements finally with respect to each other. Even after the removal of the elastic tensioning element, the surgical fixing device remains in its position, whether because the first engaging element has dug into the adjacent bone parts and is thereby fixed, or because the operating surgeon is securely holding the fixing device by a suitable handling instrument on the tensioning device.

The elastic tensioning element may be held particularly advantageously on the tensioning device.

For example, in the case of a preferred embodiment, it may be provided that the tensioning device has at least one rod that is held on the first engaging element and passes through the second engaging element and that the elastic tensioning element is held on this rod.

In particular, it may in this case be held at the free end of this rod.

In the case of a modified embodiment, the tensioning device has two rods disposed next to each other and the elastic tensioning element comprises a bridge connecting the two rods.

Furthermore, the tensioning element may carry at least one clamping element, which releasably fixes the tensioning element on the rod or the rods. The clamping element holds the elastic tensioning element on the rod or the rods in such a way that the elastic tensioning of the supporting surface on the one hand and the first engaging element on the other hand with respect to each other is ensured, but the clamping force is nevertheless only at such a level that the elastic tensioning element can be drawn away from the rod or the rods when the engaging elements are to be tensioned with respect to each other.

In the case of a preferred embodiment, the tensioning element has a spring arm which connects the supporting surface and the location where said element is connected to the tensioning device and is brought laterally past the second engaging element.

The tensioning element may carry a grip extending beyond the tensioning device, so that the operating surgeon can grasp the elastic tensioning element at this grip and optionally remove the elastic tensioning element before the tensioning of the engaging elements.

In the case of a further preferred embodiment, it is provided that the elastic tensioning element is supported on the second engaging element.

In particular, the elastic tensioning element may be pushed laterally in between the upper side of the bone parts and the underside of the second engaging element, and be able to be pushed laterally out again, when the fixing device is engaging the bone parts. In this case, the elastic tensioning element is therefore not permanently connected to the fixing device, but instead is formed as a separate part which is pushed in between the second engaging element and the upper side of the bone parts and thereby keeps the fixing device resiliently in the engaging position.

In particular, the elastic tensioning element may be a bow spring, but it would also be possible in the case of all embodiments for other types of spring to be used, for example helical springs, cup springs, cushions of elastic material, etc.

It is particularly advantageous if the bow spring is formed in a U-shaped manner, with a first arm that forms the supporting surface and a second arm that can be applied to the second engaging element and with a resilient cross-piece that connects the two arms.

A particularly advantageous arrangement is obtained if the tensioning device has at least one rod that is held on the first engaging element and passes through the second engaging element and if the elastic tensioning element is disposed on both sides of the rod or rods. In this way, an elastic pre-fixing of the fixing device is obtained in the same way, irrespective of whether the corresponding bone part is pushed in on the left-hand side or the right-hand side of the fixing device.

The elastic tensioning element may have for example a slit-shaped cut-out, which is entered by the rod or rods of the tensioning device when the elastic tensioning element is pushed in. As a result, an alignment of the elastic tensioning element is obtained at the same time, since the slit-shaped cut-out acts a guide for the elastic tensioning element.

It is advantageous if at least one arresting member is provided, which member secures the elastic tensioning element to prevent it from being pushed out in the pushed-in state, and if the arresting member can be released by displacing forces exceeding a limit value. Consequently, although the pushed-in elastic tensioning element is fixed in the pushed-in position, it can be pulled out from the engaging position by a relatively great force.

For example, the arresting member may be formed by interengaging projections and recesses on the elastic tensioning element and on the second engaging element.

It is also advantageous if the supporting surface is formed such that it rises up at its edge that is at the front during pulling out. That facilitates the pulling out of the elastic tensioning element, since the upwardly rising edge, for example a bent-up edge, acts as a slide-on surface.

In a similar way, slide-on surfaces that make it easier for the bone parts to be pushed in between the supporting surface and the first engaging element may be located on the side edges of the supporting surfaces.

It is advantageous also in the case of an elastic tensioning element that can be released in this way if it carries a grip that extends laterally beyond the second engaging element in the pushed-in state of the elastic tensioning element. This grip allows the tensioning element to be grasped and can be used to pull the tensioning element out from its tensioning position between the bone parts and the second engaging element.

In the case of a further preferred embodiment, it is provided that the supporting surface is formed by the second engaging element.

In this case, the second engaging element must be tensioned by the elastic tensioning element with respect to the first engaging element, and in this case too all elastic spring elements that are in principle familiar to a person skilled in the art can be used.

It is advantageous if a stop is provided, which stop limits the extent to which the two engaging elements come together under the action of the elastic tensioning element, so that the two engaging elements are not completely pushed together by the elastic tensioning element. This is important, since in this way the operating surgeon has the possibility of pushing the two engaging elements elastically apart for application to the bone part and of positioning the bone part between the engaging elements.

The elastic tensioning element may for example comprise at least one elastically extensible pull member, which acts on the two engaging elements and draws them elastically toward each other.

In this case, the pull member may be in the form of a closed loop and enclose the two engaging elements outwardly. It is also possible for the pull member to be disposed between the two engaging elements and fixed by in each case one end on a respective engaging element.

Pull members of this type may be formed by rubber rings, rubber filaments or similar structures, but also by helical springs and other elastically extensible pull members.

In the case of a further preferred configuration, the elastic tensioning element engages the upper side of the second engaging element and is supported on the tensioning device. In this case, the elastic tensioning element is elastically compressed or deformed and thereby exerts tensioning forces on the second engaging element.

Therefore, the elastic tensioning element may be formed for example by at least one resilient part of the second engaging element, which is supported on the tensioning device. This may, for example, take the form of one or more spring tongues cut out from the second engaging element.

In the case of a preferred configuration, the tensioning element has at least one rod that is held on the first engaging element and passes through the second engaging element and a supporting member for the elastic tensioning element is held on this rod.

This may, for example, take the form of a tensioning disk that is displaceable on the rod only in the direction of the two engaging elements and permanently tensions the two engaging elements with respect to each other in the applied state of the fixing device.

In the case of another exemplary embodiment, the supporting member may also be disposed at the free end of the rod, for example it may be releasably fitted or screwed onto the end of the rod.

The elastic tensioning element may be formed in particular as a helical spring surrounding the rod.

It is advantageous if the engaging elements carry pointed fixing projections that point in the direction of the respective other engaging element, and by which they enter the substance of the bone and are thereby held on the bone parts.

The fixing projections may be inclined with respect to the tensioning device of the two engaging elements. In this case, it is advantageous if the fixing projections are inclined toward each other, that is to say if the spacings between the fixing projections at the engaging elements are greater than the spacings at the free ends of the fixing projections. This makes it easier for the bone parts to be pushed laterally in between the engaging elements.

BRIEF DESCRIPTION OF THE DRAWINGS

The following description of example embodiments of the invention serves for further explanation in conjunction with the drawings, in which.

DETAILED DESCRIPTION

The ensuing detailed description provides exemplary embodiments only, and is not intended to limit the scope, applicability, or configuration of the invention. Rather, the ensuing detailed description of the exemplary embodiments will provide those skilled in the art with an enabling description for implementing an embodiment of the invention. It should be understood that various changes may be made in the function and arrangement of elements without departing from the spirit and scope of the invention as set forth in the appended claims.

The fixing device 1 represented in the drawing serves for connecting two bone parts 2, 3 lying next to each other, which are only represented very schematically in the drawing. These may be two plate-shaped parts of the cranial bone, two parts of the sternum separated from each other by a saw cut or similar bone parts that are to be fixed in relation to each other while lying side by side, leaving a narrow interspace 4 between the two bone parts 2, 3.

The fixing device 1 comprises a rectangular, first engaging plate 5 and a second, likewise rectangular engaging plate 6. Both engaging plates carry on their longitudinal edges. tooth-shaped projections 7 that point toward the other engaging plate, respectively, protrude substantially transversely from the planar engaging plates, penetrate into the bone material when the engaging plates 5, 6 are tensioned against the bone parts 2, 3 and secure the engaging plates 5, 6 against lateral displacement in relation to the bone parts 2, 3.

To fix the bone parts 2, 3, the first engaging plate 5 is applied to the underside of the bone parts 2, 3, to be precise in such a way that it bridges the interspace 4, and in the same way the second engaging plate 6 is applied to the upper side of the bone parts 2, 3. When the two engaging plates 5, 6 are strongly tensioned with respect to each other in this position, the two bone parts 2, 3 are fixed with respect to each other.

The first engaging plate 5 carries two tensioning rods 8, 9 that are disposed in parallel next to each other and extend perpendicularly in relation to the engaging plate, are disposed on the longitudinal center line of the first engaging plate 5 and protrude outward through the interspace 4 when the fixing device 1 is applied, the width of the interspace 4 preferably being determined by the diameter of the tensioning rods 8, 9.

Figure 1:
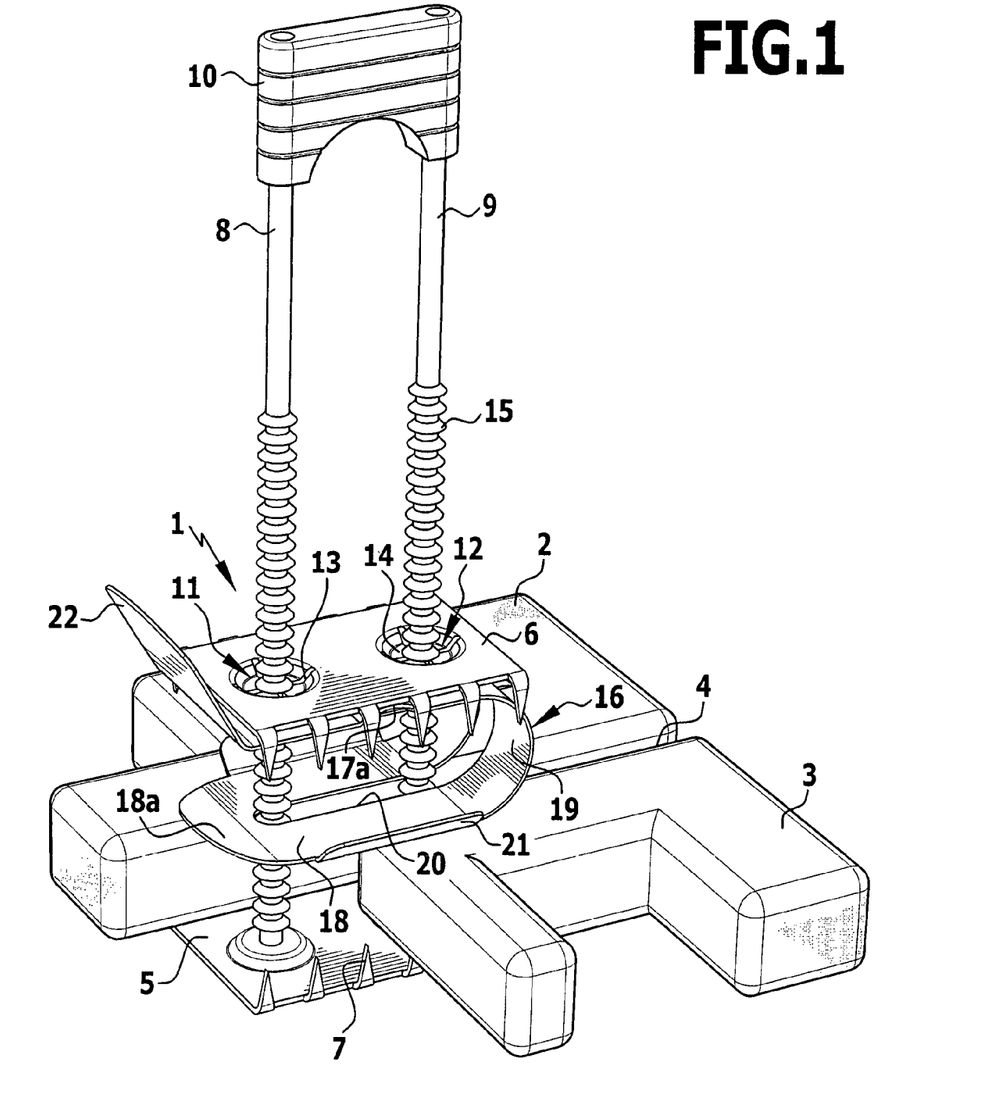
FIG. 1 shows a perspective view of a first preferred exemplary embodiment of a fixing device, with a bow spring pushed in between the bone parts and the second engaging element.
Figure 2:
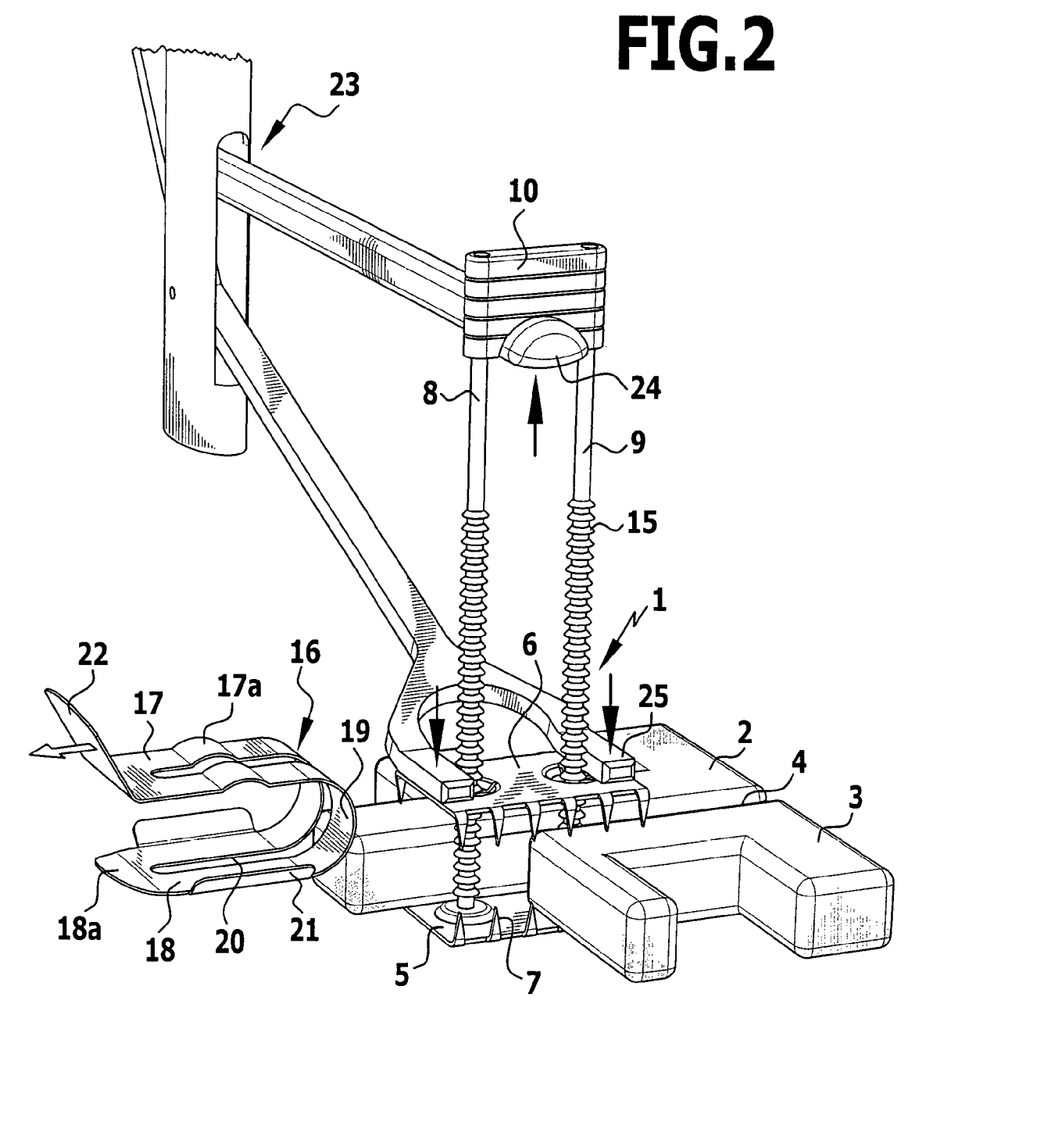
FIG. 2 shows a view similar to FIG. 1, with the bow spring pulled out and with a schematically represented device for tensioning the two engaging elements with respect to each other.

In the case of the exemplary embodiment represented in FIGS. 1 and 2, the two tensioning rods 8, 9 are connected to each other at their free end by a bridge 10, which is held axially in a non-displaceable manner on the tensioning rods 8, 9, for example by crimping.

The tensioning rods 8, 9 pass through the second engaging plate 6, which for this purpose has two apertures 11, 12. The edges of these apertures 11, 12 are subdivided into elastic tongues 14 by radial incisions 13. These tongues 14 bend back elastically when the second engaging plate 6 is displaced in the direction of the first engaging plate 5, while at the same time these tongues 14 slide along on circumferential ribs 15, which are located on the two tensioning rods 8, 9. This makes it possible to displace the second engaging plate 6 in the direction of the first engaging plate 5, but not in the reverse direction, since the tongues 14 prevent a return movement once they have bent back elastically.

To apply the fixing device of FIGS. 1 and 2 to a bone part 2, 3, the second engaging plate 6 is at first displaced only a little in the direction of the first engaging plate 5, so that the spacing between the two engaging plates 5, 6 is much greater than the thickness of the bone parts 2, 3 to be fixed. The fixing device 1 is at first positioned on one of the two bone parts 2 or 3 in such a way that the first engaging plate 5 adopts the desired position, and then a bow spring 16 is pushed into the interspace between the upper side of this bone part and the underside of the second engaging plate 6. This bow spring 16 consists of an elastically resilient strip material and is bent in a U-shaped manner, so that it has two parallel arms 17, 18 and a cross-piece 19, which is bent substantially in the form of a circle and connects these two arms 17, 18. The lower arm is bent back downward at its free end in the form of a slide-on surface 18a.

Along the bow spring 16, the latter has a central slit 20, which extends through the entire cross-piece 19 into both arms 17, 18 and the width of which is at least as great as the diameter of the tensioning rods 8, 9. This makes it possible to push the bow spring 16 forward, with the cross-piece 19 in front, between the second engaging plate 6 and the upper side of the bone part, while at the same time the two tensioning rods 8, 9 enter the slit 20, which serves at the same time as a guide for the bow spring 16. The depth to which the spring is pushed in is defined by the end of the slit 20, one of the two tensioning rods 8, 9 butting against this end of the slit 20 when the bow spring 16 has been pushed in completely (FIG. 1).

With a suitable spacing between the second engaging plate 6 and the first engaging plate 5, this elastically compressible bow spring 16 tensions the first engaging plate 5 against the underside of the bone part, i.e. the bone part is tensioned between the lower arm 18 of the bow spring 16 and the first engaging plate 5 (FIG. 1). The spacing between the two engaging plates 5, 6 can in this case be set in a suitable way by displacement of the second engaging plate 6 in the direction of the first engaging plate 5, so that as a result the spring force with which the fixing device 1 is held on the bone part can optionally also be set appropriately.

After the fixing of the fixing device 1 on one of the two bone parts 2, the other bone part 3 can then be pushed laterally into the interspace between the lower arm 18 of the bow spring 16 and the first engaging plate 5, until the bone part butts against the tensioning rods 8, 9. The lower arm 18 of the bow spring 16 is thereby pressed resiliently upward, so that the bone part can also slide past the protruding projections 7.

These projections 7 may extend perpendicularly from the two engaging plates 5, 6, but it is also possible to incline these projections 7 slightly inward, as can be seen in particular from FIGS. 5 to 9. This makes it easier for the bone parts to be introduced between the first engaging plate 5 and the bow spring 16.

In a similar way, a sloping run-in surface 21 may be respectively provided on the side edges of the lower arm 18 of the bow spring 16, which surface slides along on the bone parts when the bone parts 2, 3 are pushed toward each other, and thereby resiliently raises the lower arm 18 (FIGS. 1 and 2).

The fixing device 1 is pressed by the bow spring 16 against the bone parts 2, 3 in such a way that the first engaging plate 5 engages with its projections 7 in the bone parts 2, 3, and thereby provides fixing of the fixing device on the bone parts 2, 3. It is therefore possible to remove the bow spring 16 again after this fixing, which is effected simply by pulling it out laterally. For this purpose, the bow spring 16 carries a grip 22 in the form of an obliquely upwardly bent lobe, by which the bow spring 16 can be grasped by hand or by means of an instrument and then pulled out. Although this brings an end to the elastic tensioning force, the fixing device remains in this position, since it is kept in this position by the projections 7 digging into the bone material. After removal of the bow spring 16, it is possible to tension the two engaging plates 5 and 6 with respect to each other by a tensioning instrument 23 that is only represented very schematically in FIG. 2. For this purpose, the tensioning instrument 23 engages a bridge 10 with an upper tensioning tool 24 and engages the upper side of the second engaging plate 6 with a lower tensioning tool 25. When the two tensioning tools 24 and 25 spread apart, the second engaging plate 6 is thereby displaced in the direction of the first engaging plate 5 along the two tensioning rods 8, 9, and this leads to a final fixing of the two engaging plates 5, 6 on the bone parts 2, 3 (FIG. 2). After that, the projecting parts of the tensioning rods 8, 9 can be removed, for example with the aid of a cutting tool, and the fixing device 1 remains in the body. On the other hand, the removed upper parts of the tensioning rods 8, 9 with the bridge 10 and the bow spring 16 are removed from the operating area.

The upper arm 17 of the bow spring 16 is convexly curved upward in its middle region between the cross-piece 19 and its end (FIG. 2), this convexity 17a engaging between the two apertures 11, 12, which protrude slightly downward beyond the second engaging plate 6, when the bow spring 16 has been pushed in completely. This engagement of the convexity 17a between the two downwardly protruding apertures 11, 12 provides fixing of the bow spring 16 against displacement in the direction of the slit 20, i.e. the bow spring 16 is fixed in the pushed-in state. However, this fixing can be released by pulling strongly on the grip 22, as a result of which the convexity 17a slides up on the downwardly protruding aperture 11 and bends the upper arm 17 elastically downward, so that the bow spring 16 can be pulled out completely from the interspace between the bone part and the upper engaging plate 6.

Figure 3:
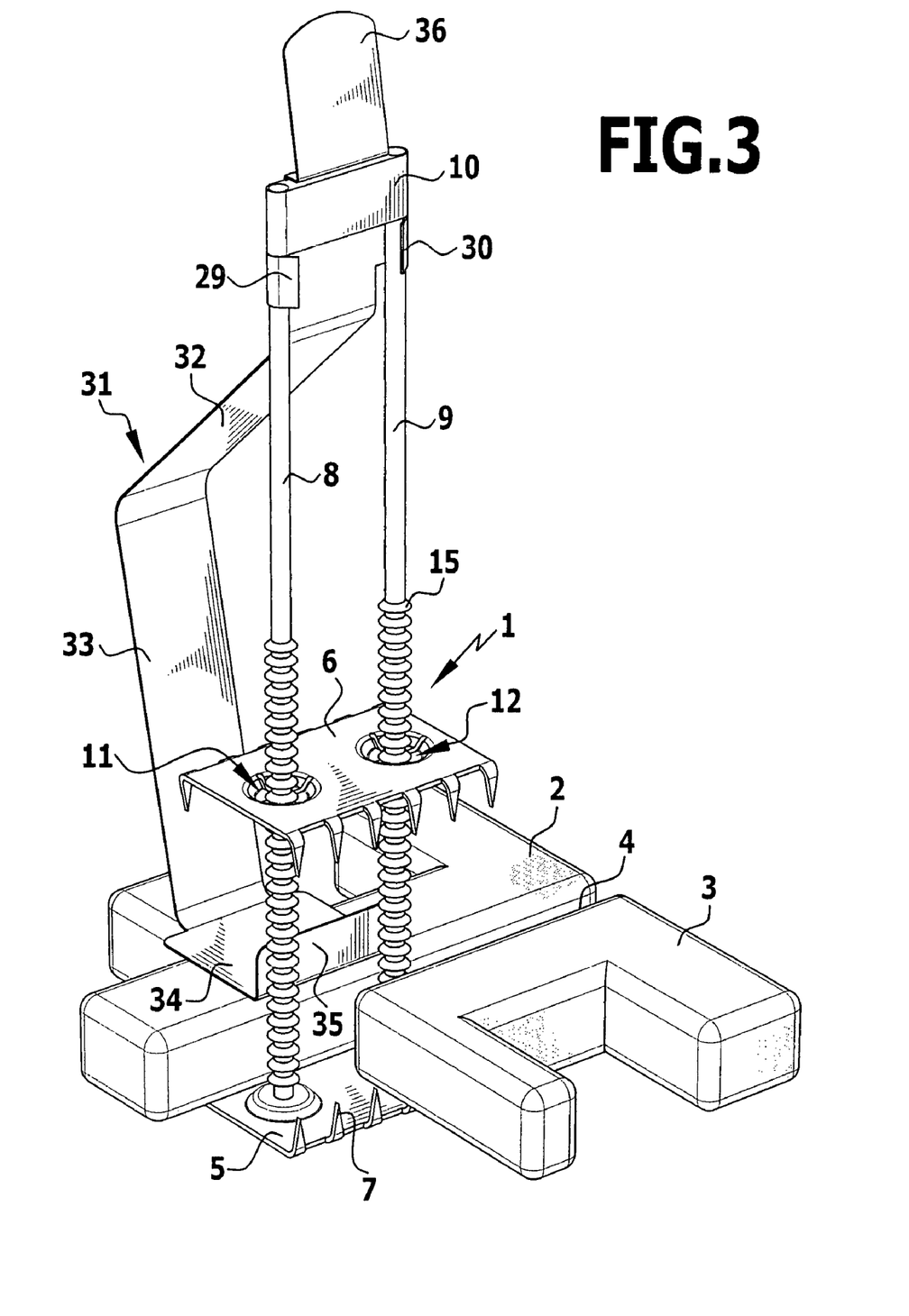
FIG. 3 shows a view similar to FIG. 1 in the case of a further exemplary embodiment of a fixing device, with an elastic tensioning element held on tensioning rods.
Figure 4:
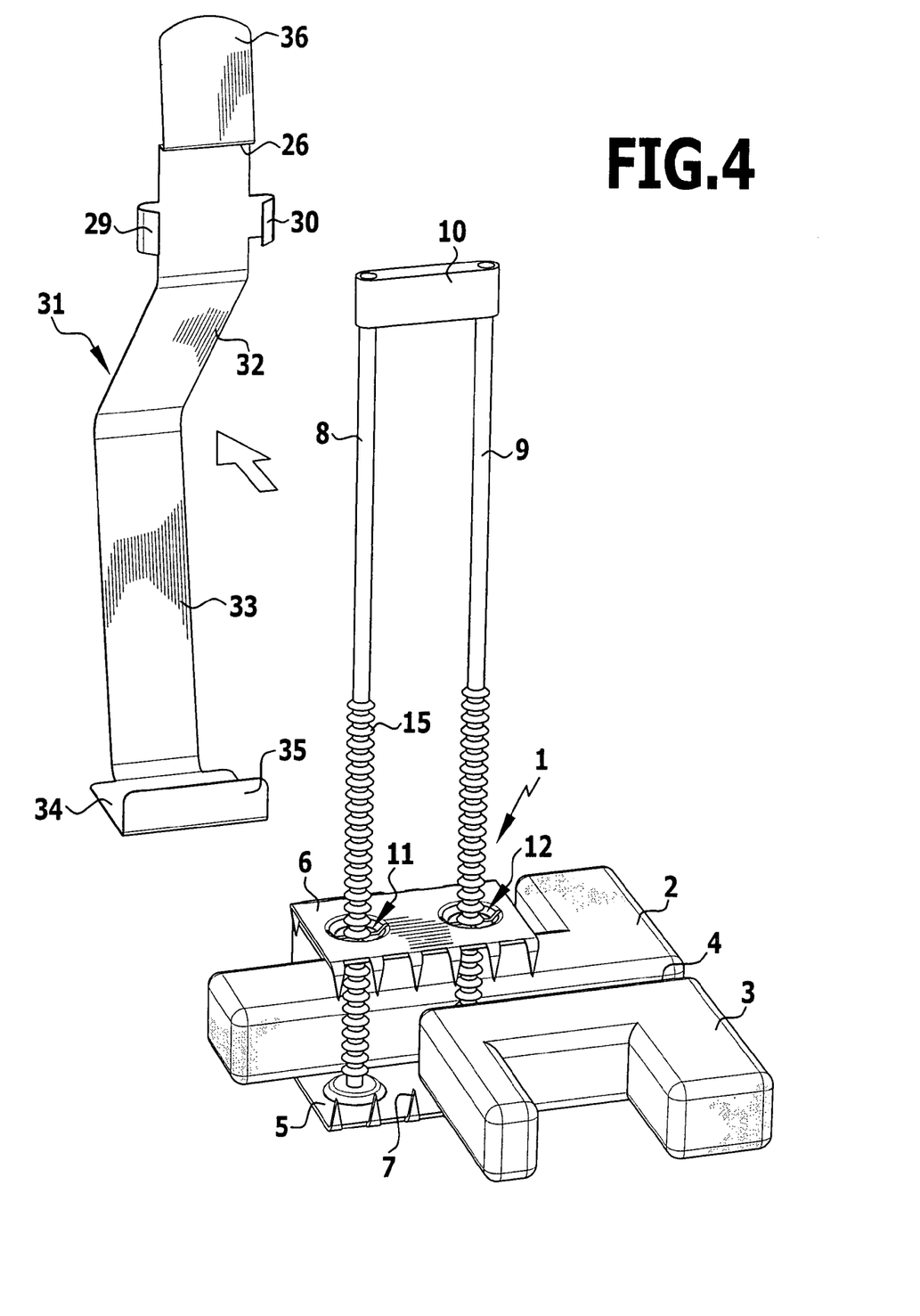
FIG. 4 shows a view similar to FIG. 3 after removal of the elastic tensioning element and before the fitting-on of a bridge for connecting the two tensioning rods.

In the case of the exemplary embodiment represented in FIGS. 3 and 4, a similar structure has been chosen, so parts that correspond to one another have the same designations.

On the two rods 8, 9 of the fixing device 1, which are connected to each other at their free end by way of a bridge 10, a spring arm 31 is releasably held, to be precise with the aid of two clamping members 29 and 30, which partly grip around the tensioning rods 8, 9. The spring arm consists of an elastically bendable material in strip form and has a step 26, which rests on the upper side of the bridge 10 when the spring arm 31 is connected to the fixing device 1. The spring arm 31 has two straight portions 32 and 33, connected to each other at an angle, and, at its lower end, the spring arm 31 goes over into a supporting plate 34, which runs parallel to the two engaging plates 5, 6, is located between the two engaging plates 5, 6 and has on its longitudinal edge opposite the spring arm 31 an edge region 35 protruding upward at a right angle.

On account of the elastic properties of the spring arm 31, the supporting plate 34 can be moved away from the first engaging plate 5 against the spring force of the spring arm 31, so that the fixing device 1 can be applied to a bone part in such a way that the latter is tensioned between the supporting plate 34 and the first engaging plate 5. The spring arm 31 thereby presses the supporting plate 34 resiliently against the upper side of the bone part and thereby tensions the first engaging plate 5 against the underside of the bone part, it being possible for the tooth-shaped projections 7 to penetrate at least partially into the bone material. In this way, fixing of the fixing device 1 on the bone part is possible, the second engaging plate 6 still remaining at a distance above the bone parts 2, 3 (FIG. 3).

In a way similar to in the case of the exemplary embodiment of FIGS. 1 and 2, the second bone part can then be pushed laterally in between the supporting plate 34 and the first engaging plate 5.

Before the two engaging plates 5, 6 are finally tensioned securely with respect to each other, the spring arm 31 is removed. For this purpose, the clamping elements 29, 30 are bent up. The releasing operation is assisted by an upwardly protruding extension 36 in lobe form, by which the spring arm 31 can be grasped.

After the removal of the spring arm 31, the engaging plates 5, 6 can be finally tensioned with respect to each other in a way similar to in the case of the exemplary embodiment of FIG. 2.

In the case of the exemplary embodiments of FIGS. 1 to 4, the first engaging plate 5 is tensioned against a bone part by means of a tensioning surface; in the exemplary embodiment of FIGS. 1 and 2 the lower arm 18 forms the tensioning surface, in the exemplary embodiment of FIGS. 3 and 4 the supporting plate 34 forms the tensioning surface.

By contrast with this, configurations in which such a tensioning surface is formed by the second engaging plate 6 itself are represented in FIGS. 5 to 9. In these cases, care is taken that the two engaging plates 5, 6 are tensioned elastically with respect to each other, thereby making it possible for the fixing device 1 to be fixed on a bone part.

The fixing devices 1 represented in FIGS. 5 to 9 are constructed in a way similar to those of FIGS. 1 to 4, so parts that correspond to one another have the same designations. By contrast with the exemplary embodiments of FIGS. 1 to 4, in the case of the exemplary embodiments of FIGS. 5 to 9 only a single tensioning rod 8 is provided, but it would be quite possible also to provide these exemplary embodiments with two tensioning rods in a way similar to that represented in the case of the exemplary embodiments of FIGS. 1 to 4.

Figure 5:
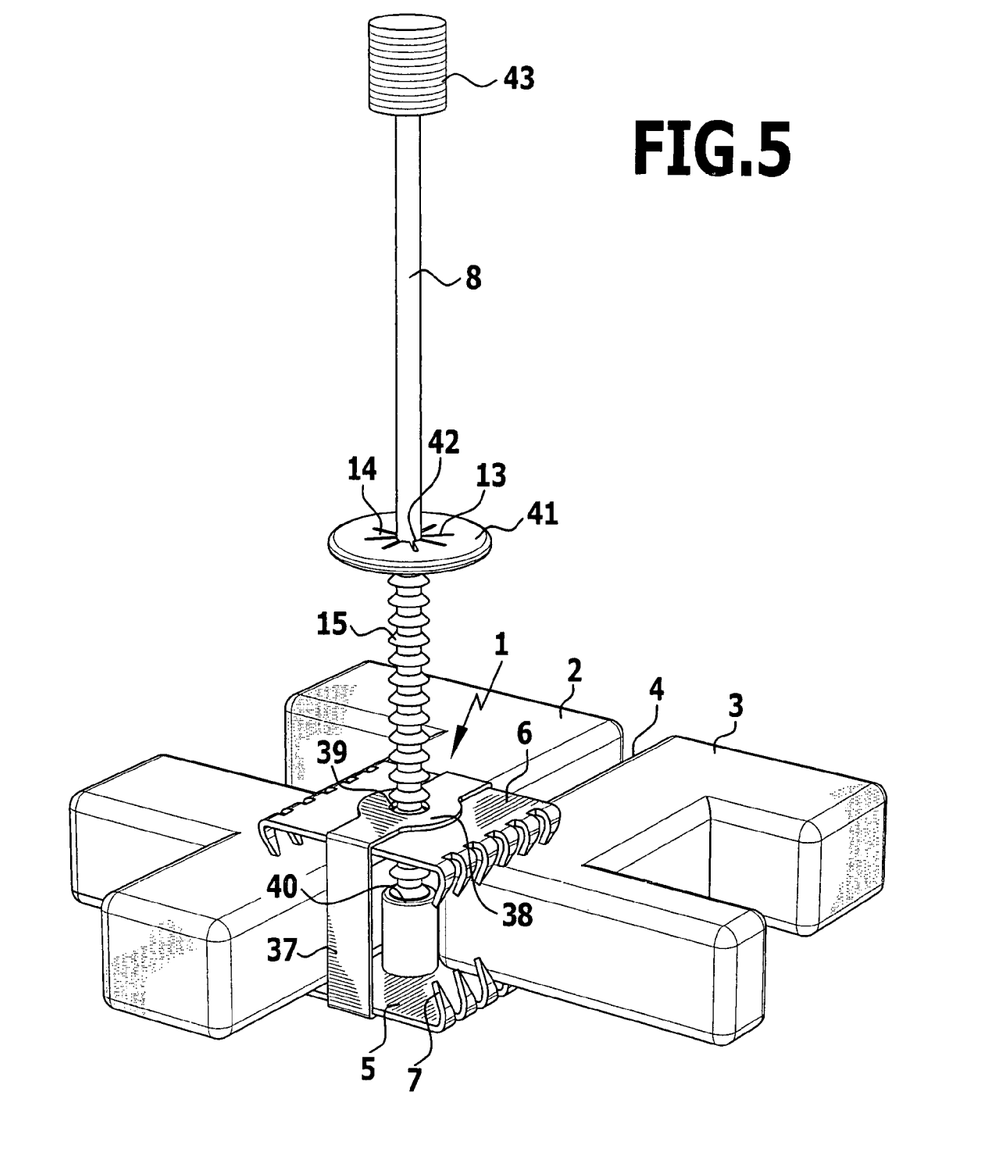
FIG. 5 shows a view similar to FIG. 1 in the case of a further preferred exemplary embodiment of a fixing device, with an elastically extensible tensioning element surrounding the two engaging elements.

In the case of the exemplary embodiment of FIG. 5, the two engaging plates 5, 6 are surrounded by an elastic band 37, which is in the form of a closed loop, is brought past the outside of said plates and in the simplest case is a rubber ring or a comparable elastic component of a material that is tolerated by the body, for example of silicone. For the fixing of this band 37, it has a widening 38 with an opening 39, which lies directly over the aperture 11 of the second engaging plate 6, so that the tensioning rod 8 also passes through this opening 39.

The two engaging plates 5, 6 are elastically tensioned with respect to each other by this band 37, while a stepped widening 40 of the tensioning rod 8 prevents them from coming together completely under the action of the elastic band 37, this stepped widening 40 directly abutting the first engaging plate 5 and forming a stop for the second engaging plate 6.

In the case of the exemplary embodiment of FIG. 5, the second engaging plate 6 is freely displaceable on the tensioning rod 8 in both directions, so does not have the radial incisions 13 and the tongue 14 that are provided in the case of the exemplary embodiments of FIGS. 1 to 4. This makes it possible to increase the spacing between the two engaging plates 5, 6 against the action of the elastic band 37 and adapt it to the thickness of the bone parts.

For the final tensioning of the two engaging plates 5, 6 with respect to each other, an arresting disk 41 is mounted on the tensioning rod 8 and has a central opening 42, through which the tensioning rod 8 passes. This opening 42 is formed in a way similar to the aperture 11 in the case of the exemplary embodiments of FIGS. 1 to 4, because radial incisions 13 are provided, which incisions subdivide the arresting disk 41 in the edge region of the opening 42 into a number of resilient tongues 14 lying next to one another. In this way, the arresting disk 41 can be displaced from above downward, but because of the circumferential ribs 15 cannot be displaced from below upward, in a way similar to the second engaging plate 6 in the case of the exemplary embodiments of FIGS. 1 to 4.

The displacement of the arresting disk 41 is performed by a tensioning instrument, which is formed in a way similar to the tensioning instrument 23 in the case of the exemplary embodiment of FIG. 2; in this case, the upper tool is then supported on a head-shaped thickening 43 of the tensioning rod 8. Once the fixing device 1 has been fixed on the bone parts 2, 3, the elastic band 37 can be removed before the arresting disk 41 is displaced into the final tensioning position; the elastic band can be removed for example simply by cutting it open and pulling it laterally away.

Figure 6:
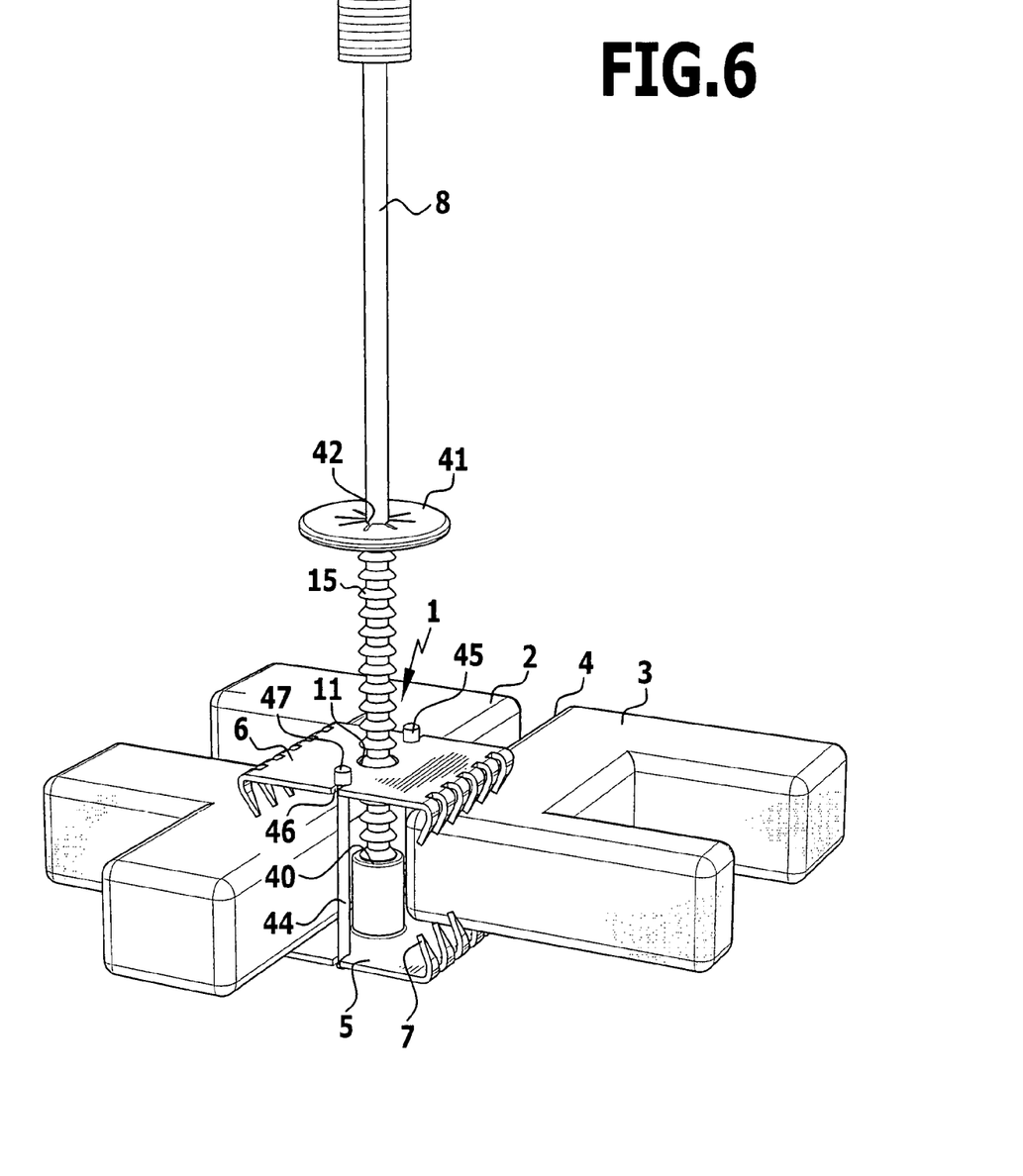
FIG. 6 shows a view similar to FIG. 5 in the case of a further preferred exemplary embodiment, with elastically extensible tensioning elements disposed between the engaging elements, elastically tensioning them with respect to each other.

In the case of the exemplary embodiment of FIGS. 6, a similar arrangement as in the case of the exemplary embodiment of FIG. 5 has been chosen; parts that correspond to one another therefore have the same designations.

In this case, the two engaging plates 5, 6 are not tensioned with respect to each other by an elastic band surrounding them, but instead by two elastic extensible tensioning elements 44, 45, which are respectively fixed by their ends on the two engaging plates 5, 6 and are disposed in the interspace between the two engaging plates 5, 6. The arrangement is chosen such that the two tensioning elements 44, 45 similarly lie in the interspace 4 of the two bone parts 2, 3.

The tensioning elements 44, 45 may be tension springs or rubber-elastic bands.

These tensioning elements 44, 45 can also be removed; in this case, removal is also possible even when the engaging plates 5, 6 are completely tensioned with respect to each other by the arresting disk 41.

The tensioning elements 44, 45 may for example be inserted into the engaging plates 5, 6 through laterally open slits 46 in the latter and are fixed in the axial direction by a head-shaped thickening 47. This makes it possible to pull the tensioning elements 44, 45 laterally out from these slits 46 and in this way release them from the engaging plates 5, 6 if the tensioning elements 44, 45 are to be removed.

Figure 7:
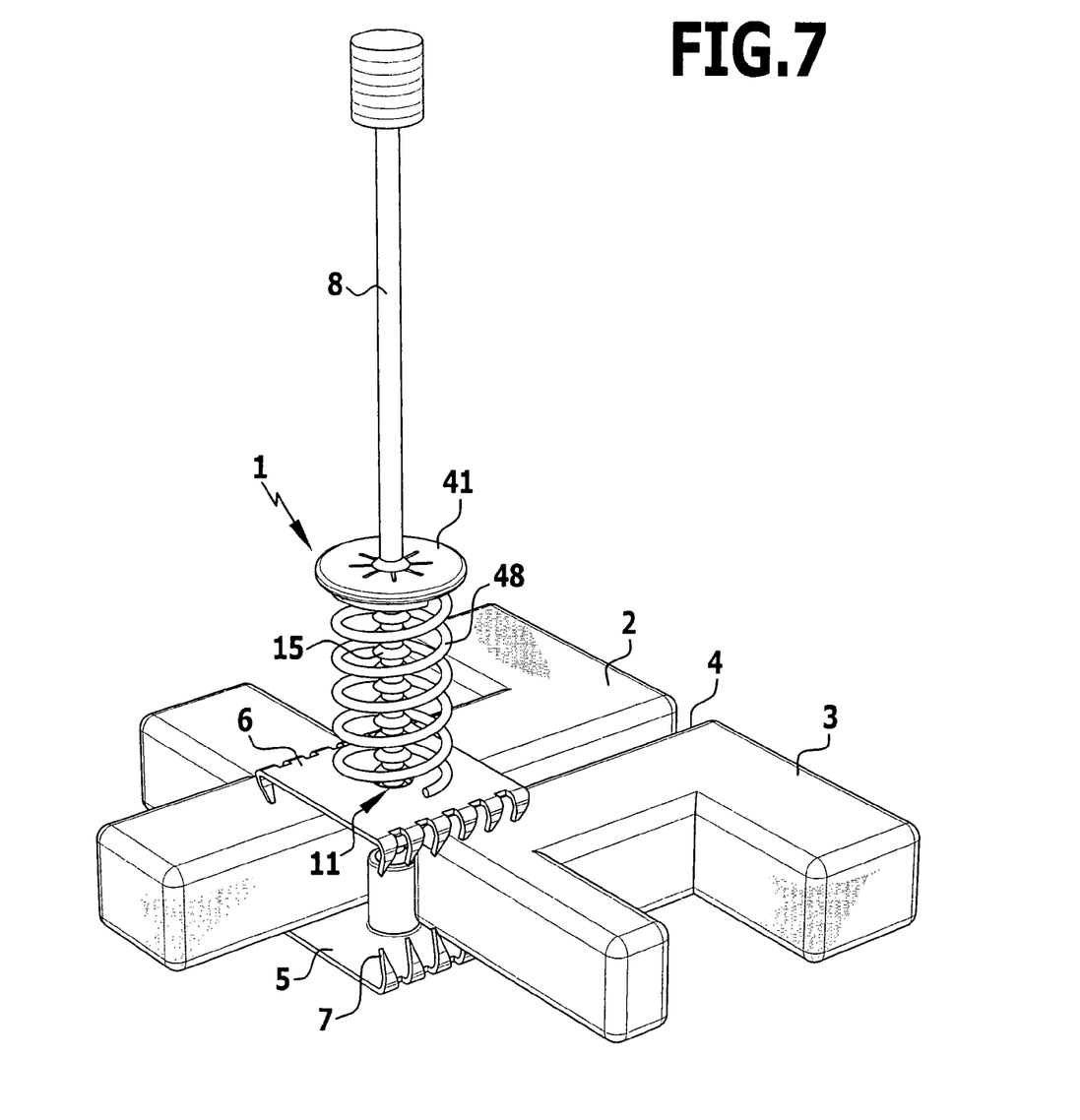
FIG. 7 shows a view similar to FIG. 5, with a helical spring surrounding a tensioning rod for elastically tensioning the two engaging elements with respect to each other.

In the case of the exemplary embodiment of FIG. 7, a structure similar to in the case of the exemplary embodiment of FIG. 5 has been chosen, so parts that correspond to one another have the same designations.

In this case, the two engaging plates 5, 6 are not tensioned with respect to each other by an elastic band but instead by a helical spring 48, which concentrically surrounds the tensioning rod 8 and is supported on the one hand on the upper side of the second engaging plate 6 and on the other hand on the underside of the arresting disk 41, and as a result displaces the second engaging plate 6 elastically toward the first engaging plate 5.

In the case of this exemplary embodiment, in the final tensioning together of the engaging plates 5, 6 this helical spring 48 is completely compressed, but it would also be possible to remove this helical spring 48, for example by the helical spring 48, which is wound from thin spring wire, being pulled off laterally, so that the spring wire is stretched.

Figure 8:
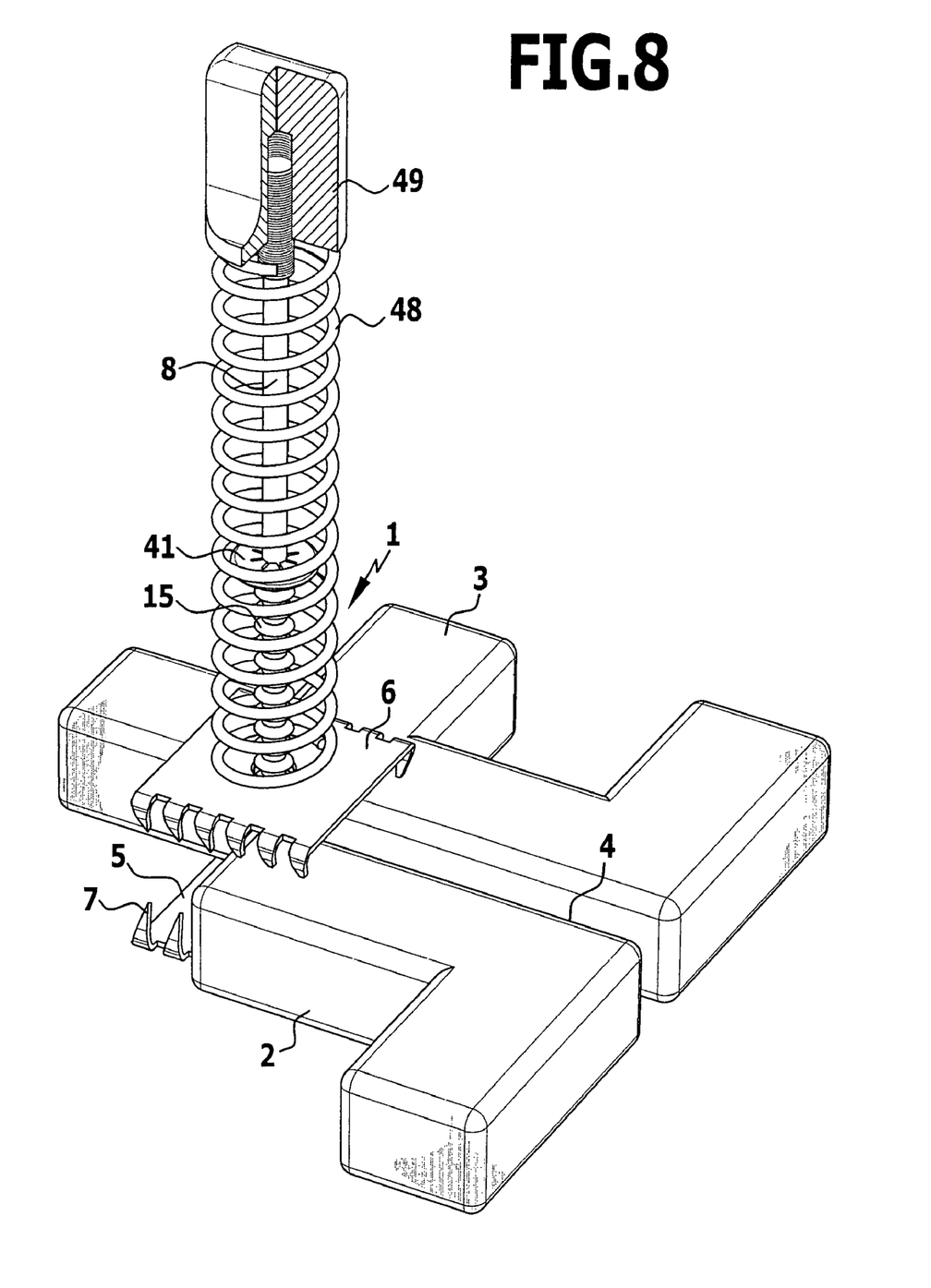
FIG. 8 shows a view similar to FIG. 7, with a helical spring surrounding a tensioning rod and a support at the free end of the tensioning rod.

A similar configuration is realized in the case of the exemplary embodiment of FIG. 8.

As a difference from the exemplary embodiment of FIG. 7, the helical spring 48 in the case of this exemplary embodiment surrounds the arresting disk 41 at a spacing and is supported on a stop 49, which is fitted on the free end of the tensioning rod 8. The stop 49 may be held for example in a clamping fit on the tensioning rod 8 or by a thread onto which the stop 49 is screwed, or by a bayonet fastening. This makes it possible to remove the stop 49 after positioning the fixing device 1 on the bone parts and to pull the helical spring 48 off upward, so that the tensioning rod 8 and the arresting disk 41 are exposed in the way that can be seen from FIGS. 5 to 7. The stop 49 can be fitted again onto the tensioning rod 8 and then acts in a way similar to the head-shaped thickening 43 as a stop for a tensioning instrument.

Figure 9:
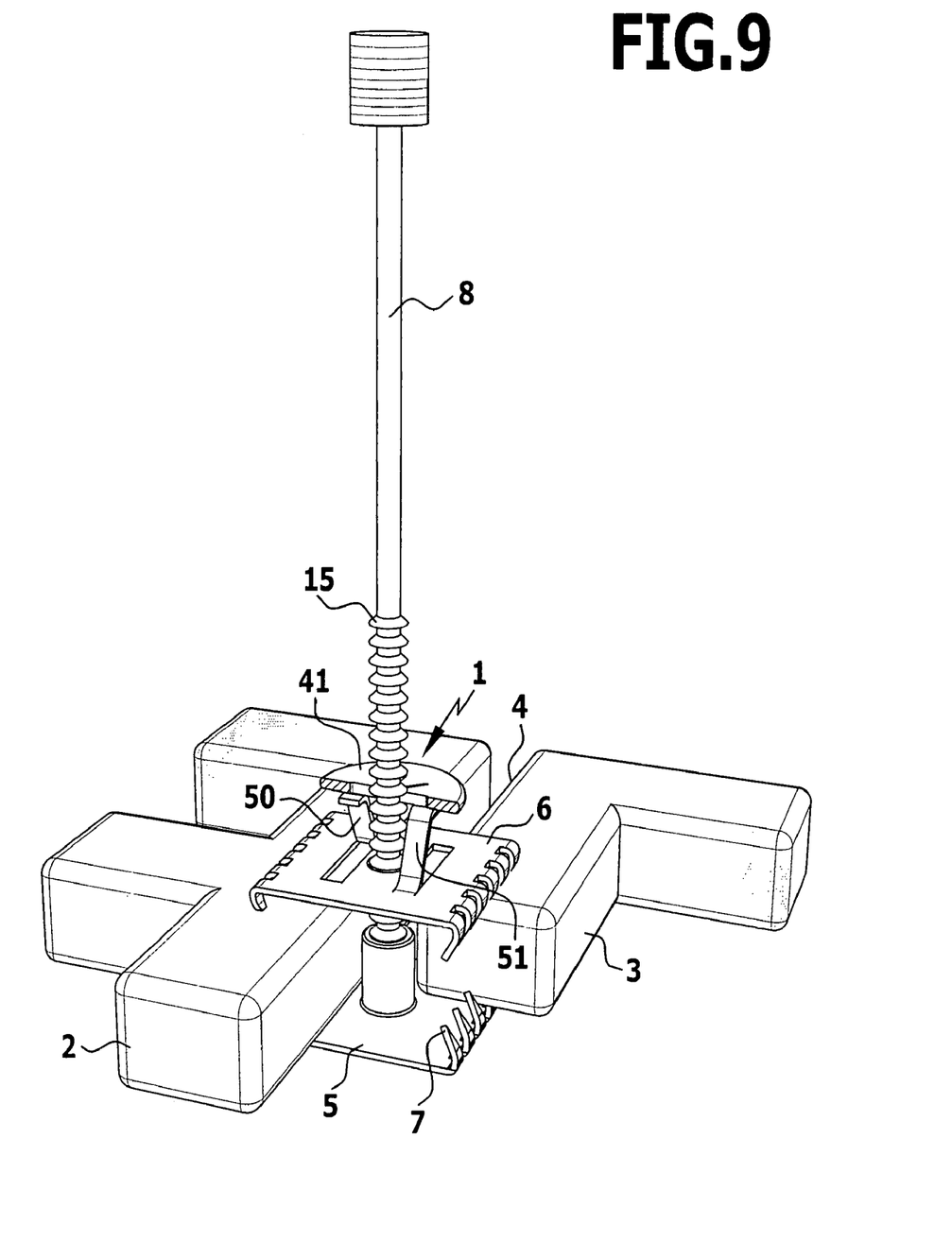
FIG. 9 shows a view similar to FIG. 7, with spring tongues in the second engaging element for elastically tensioning the two engaging elements with respect to each other.

In the case of the exemplary embodiment of FIG. 9, which is constructed in a way similar to that of FIG. 5 and in which the same parts again have the same designations, tongue-shaped regions have been punched out from the second engaging plate 6 by U-shaped cuts, have been bent upward and form the spring tongues 50, 51. These are supported on the arresting disk 41 and thereby tension the engaging plates 5, 6 resiliently with respect to each other. The spacing can in this case be increased against the spring force of these spring tongues 50, 51, so that the fixing device 1 can be pushed laterally onto the bone parts or the bone parts can be pushed in between the engaging plates 5, 6. For the final tensioning of the engaging plates 5, 6, the arresting disk 41 is displaced downward and thereby at the same time also bends the spring tongues 50, 51 downward to such an extent that the arresting disk 41 comes to lie on the upper side of the second engaging plate 6.

It should now be appreciated that the present invention provides advantageous methods and apparatus for the fixing together of adjacent bone parts.

Although the invention has been described in connection with various illustrated embodiments, numerous modifications and adaptations may be made thereto without departing from the spirit and scope of the invention as set forth in the claims.

What is claimed is:

1. A Surgical fixing device for the fixing together of two adjacent bone parts, comprising:
    a first engaging element for engaging an underside of the two bone parts; a second engaging element for engaging an upper side of the two bone parts; a tensioning device adapted to connect the two engaging elements to each other through an interspace between the bone parts and to permanently fix the two engaging elements with respect to each other in a tensioned manner when the first and second engaging elements respectively engage the underside and the upper side of the bone parts; and at least one elastic tensioning element adapted to displace a supporting surface of the elastic tensioning element applied to the upper side of the bone parts toward the first engaging element for tensioning the first engaging element to the underside of one of the two bone parts, the supporting surface and the first engaging element are moveable away from each other against the force of the elastic tensioning element, wherein the supporting surface is disposed between the two engaging elements before the fixing device is applied to the bone parts, and wherein the elastic tensioning element is releasably connected to the fixing device.

2. Fixing device in accordance with claim 1, wherein the elastic tensioning element is held on the tensioning device.

3. Fixing device in accordance with claim 2, wherein:
the tensioning device has at least one rod that is held on the first engaging element, extends through said interspace, and passes through the second engaging element; and
the elastic tensioning element is held on said at least one rod.

4. Fixing device in accordance with claim 3, wherein the elastic tensioning element is held at a free end of the at least one rod.

5. Fixing device in accordance with claim 3, wherein:
the tensioning device has two rods disposed next to each other; and
the elastic tensioning element has a cross-piece connecting the two rods.

6. Fixing device in accordance with claim 3, wherein the elastic tensioning element carries at least one clamping element which releasably fixes the elastic tensioning element on the at least one rod.

7. Fixing device in accordance with claim 3, wherein:
the elastic tensioning element has a spring arm which connects the supporting surface and the location where said elastic tensioning element is connected to the tensioning device; and
said spring arm extends laterally past the second engaging element.

8. Fixing device in accordance with claim 3, wherein the elastic tensioning element carries a grip extending beyond the tensioning device.

9. Fixing device in accordance with claim 1, wherein the elastic tensioning element is supported on the second engaging element.

10. Fixing device in accordance with claim 9, wherein:
the elastic tensioning element is pushable laterally in between the upper side of the bone parts and an underside of the second engaging element; and
said elastic tensioning element is pushable laterally out from between the upper side of the bone parts and the underside of the second engaging element when the fixing device engages the bone parts.

11. Fixing device in accordance with claim 10, wherein:
at least one arresting member is provided, which arresting member secures the elastic tensioning element to prevent said elastic tensioning element from being pushed out when in a pushed-in state; and
the arresting member can be released by displacing forces exceeding a limit value.

12. Fixing device in accordance with claim 11, wherein the arresting member is formed by interengaging projections and recesses on the elastic tensioning element and on the second engaging element.

13. Fixing device in accordance with claim 12, wherein the supporting surface is formed such that it rises up at an edge thereof that is at a front portion of said supporting surface during pulling out from between the upper side of the bone parts and the underside of the second engaging element.

14. Fixing device in accordance with claim 10, wherein the elastic tensioning element carries a grip that extends laterally beyond the second engaging element in a pushed-in state of the elastic tensioning element.

15. Fixing device in accordance with claim 9, wherein the elastic tensioning element is a bow spring.

16. Fixing device in accordance with claim 15, wherein the bow spring is U-shaped, with a first arm that forms the supporting surface, a second arm adapted to be applied to the second engaging element, and a resilient cross-piece that connects the two arms.

17. Fixing device in accordance with claim 9, wherein:
the tensioning device has at least one rod that is held on the first engaging element, extends through said interspace, and passes through the second engaging element; and
the tensioning element is disposed on both sides of the at least one rod.

18. Fixing device in accordance with claim 17, wherein the tensioning element has a slit-shaped cut-out, which is entered by the at least one rod of the tensioning device when the elastic tensioning element is pushed in between the upper side of the bone parts and an underside of the second engaging element.

19. Fixing device in accordance with claim 1, wherein each of the engaging elements carry pointed fixing projections that point in the direction of the respective other engaging element.

20. Fixing device in accordance with claim 19, wherein the fixing projections are inclined with respect to the tensioning device of the two engaging elements.

* * * * *